United States Patent
Herweck et al.

[19]

[11] Patent Number: 5,807,358
[45] Date of Patent: Sep. 15, 1998

[54] DRY SUCTION REGULATOR BLOOD COLLECTION DEVICE

[75] Inventors: Steve A. Herweck, Nashua; Theodore Karwoski, Hollis; David Cross, Atkinson, all of N.H.

[73] Assignee: Atrium Medical Corporation, Hudson, N.H.

[21] Appl. No.: 472,144

[22] Filed: Jun. 7, 1995

Related U.S. Application Data

[63] Continuation-in-part of Ser. No. 404,108, Mar. 13, 1995, abandoned.

[51] Int. Cl.[6] .................................................. A61M 1/00
[52] U.S. Cl. ......................................... 604/320; 604/321
[58] Field of Search ................................. 604/317–326, 604/4; 137/205

[56] References Cited

U.S. PATENT DOCUMENTS

| | | | |
|---|---|---|---|
| 3,559,647 | 2/1971 | Bidwell et al. | 604/321 |
| 3,683,913 | 8/1972 | Kurtz et al. | 128/276 |
| 3,993,067 | 11/1976 | Schachet et al. | 604/4 |
| 4,465,483 | 8/1984 | Weilbacher | 604/317 |
| 4,540,413 | 9/1985 | Russo | 604/320 |
| 4,955,873 | 9/1990 | Rajlevski | 604/322 |
| 4,963,135 | 10/1990 | Kerwin | 604/321 |
| 4,988,342 | 1/1991 | Herweck et al. | 604/321 |
| 5,026,358 | 6/1991 | Everett, Jr. et al. | 604/320 |
| 5,144,416 | 9/1992 | Karwoski et al. | 604/321 |
| 5,397,299 | 3/1995 | Karwoski et al. | 604/4 |

OTHER PUBLICATIONS

ITHAT, Medi–Vac Corp., 1979.

*Primary Examiner*—John G. Weiss
*Assistant Examiner*—David J. Cho
*Attorney, Agent, or Firm*—Lahive & Cockfield

[57] ABSTRACT

A blood collection device has a modular suction regulator assembly in the form of an adjustable negative pressure relief valve which controls the level of suction in a collection chamber by admitting air to a short bleed-in passage proximate to a suction connection. The modular assembly is a canister which drops into a receptacle oriented transversely in the collection vessel, and defines a laterally-directed intake manifold which resists blockage. The intake passes centrally through the canister along a path spanned by a filter, past a hat-shaped poppet supported on a compression spring. Fluted and threaded members control the scale and range of poppet response so that the assembly may be calibrated before installation. A face plate covers the installed canister, and radial vanes in the intake manifold double as gripping elements for manual adjustment of the assembly. A bellows meter provides refined suction resolution by linearly advancing across an oblique or curved reference line. Other improvements include a compact and balanced layout of suction canister, seal chamber and collection chamber, and a rigid handle assembly having five faces integral with the device.

14 Claims, 7 Drawing Sheets

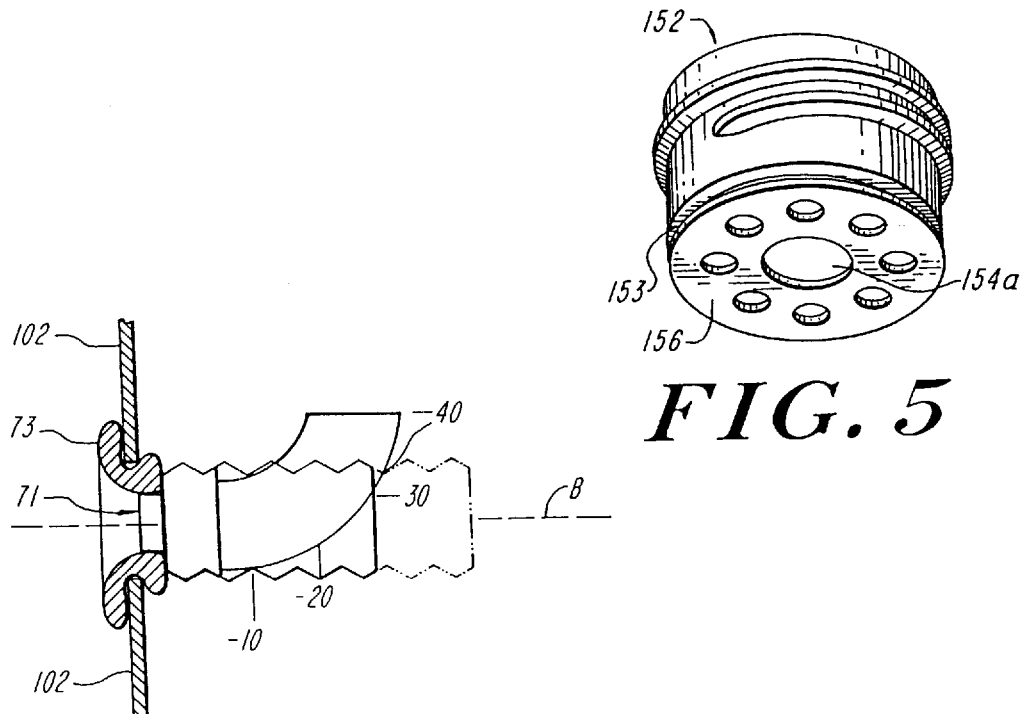
FIG. 5
FIG. 6
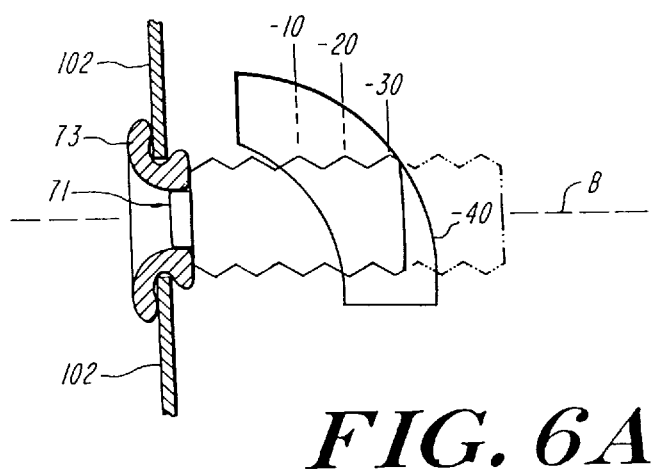
FIG. 6A

DRY SUCTION REGULATOR BLOOD COLLECTION DEVICE

REFERENCE TO RELATED APPLICATIONS

This application is a continuation-in-part of Applicant's; earlier-filed U.S. patent application U.S. Ser. No. 08/404,108 filed on Mar. 13, 1995, now abandon the priority of which is hereby claimed. That application and the earlier patents on which it relies, including Applicant's; earlier U.S. patents identified below, are all incorporated herein by reference. This application is also related to commonly-owned U.S. patent application entitled "Filtered Blood Collection Device" which is being filed at the same time as this patent application. That patent application is also incorporated herein by reference.

BACKGROUND

The present invention relates to blood collection or autoinfusion devices such as are used for postoperative and intraoperative blood collection to collect bleeding and fluid loss from a patient. These devices have evolved over the last several decades from two basic lines of medical instruments. The first form of device, a cardiotomy reservoir, is a bottle or bucket assembly operating much like a vacuum cleaner, and used to collect blood during cardiac surgery. These devices are generally large unobstructed covered vessels which connect to a vacuum supply and have a suction wand to suck up loose pools of blood within the operating arena. The second form of device, generally referred to as a chest drain, is a relatively compact bedside vessel used to collect fluids postoperatively from a closed surgical site, e.g., from a drain tube implanted in the patient's; chest. These latter devices generally operate with a much smaller magnitude of suction, in the range of −15 to −25 cm. $H_2O$, and typically include either a dry or wet suction regulator mechanism, as well as a water seal or one-way valve which prevents direct entry of atmospheric air into the blood collection chamber of the drain device. Since these devices apply their suction to the chest cavity and may be acted on by, or may affect motion of the lungs within the chest cavity, they generally also contain various forms of release valve to prevent excessive levels of either pressure or suction from occurring in the collection portion of the vessel or being applied to patient drain line.

Chest drain mechanisms, whether wet or dry, pose several special design problems. In general, since they apply suction directly to a patient's; chest cavity, they must be capable of providing a low and consistent suction level compatible with human breathing cycles. On the other hand, the thoracotomy tube which connects them to a drainage site in a patient's; chest may draw air through the tube due to a perforation in the lungs or a leaky closure of the wound site to which it is attached. Air leakage from these additional sources provides a challenge in designing a suction regulator capable of sufficiently accurate low level long term regulation.

A typical wet suction drain employing a water column of the desired 15 to 20centimeter height to bleed down the level of suction available at a regulated or unregulated hospital vacuum wall fitting, may experience drift due to evaporation of the water column. These wet drains are also prone to spillage of the water column and loss of pressure when the drain is tipped.

Traditional multi-stage suction regulators which rely on a number of small passages in series have little application to these devices since they are adapted to static suction situations in which there is relatively little flow. Instead, poppet, flap or diaphragm-type valves have generally been more effective in implementing dry suction regulator assemblies for chest drains of this type. A number of such constructions are known from the patents or products of workers in this field, such as Leonard Kurtz, Sueshiro Akiyama, the present inventors and others, as well as from non-patent medical publications. However, beyond the problem of providing a regulator structure capable of accommodating the extreme variation in conditions which occur in a hospital setting, other common nonphysical considerations related more to industrial design than to simple engineering have not been effectively addressed in these prior art structures.

Thus, for example, it would be desirable to produce a dry suction regulator which does not require special skill, training or attentiveness to set up.

It would also be desirable to produce a dry suction regulator in which the various components provide both a proper suction operation and metered confirmation of proper operation.

It would further be desirable to provide such a dry suction device of low complexity and of great ease of assembly or manufacture.

SUMMARY OF THE INVENTION

These and other desirable features are obtained in a dry suction regulation device in accordance with the present invention, such as a chest drain, wherein a large air entryway or manifold in a side wall of the device conducts air to a spring loaded poppet valve to bleed down a higher level of suction which is applied at a suction port at the top of the device. The poppet valve is adjustable and is mounted within an open-ended threaded canister in which radial fins allow air approaching laterally through the manifold to pass axially past the poppet, forming a direct, high conductance path to the suction outlet. Below the poppet valve, a water seal chamber prevents migration of outside air to the collection chamber proper, while an expansion bellows is positioned to indicate operating levels of suction in the seal chamber. The expansion bellows is also located below the level of the poppet and it expands proximate to a curved graduation contour that compensates for parallax and perspective defects encountered in the hospital room placement of the device below observation level. In a preferred embodiment, the poppet valve drops into a cup-shaped recess in the body of the device wherein it seals laterally against protruding walls to form an internal entry channel directing the admitted air to the suction connection. A filter within the canister filters air as it enters, and a face plate assembled over a broad front surface of the collection device shields or masks the inlet assembly from direct contact or from being draped over or blocked by dangling sheets or the like. The major part of the drain vessel is given over to a collection chamber, with the poppet valve, water seal, and collection chamber being compactly arranged to provide a low and generally centered center of gravity that rises slowly as the collection chamber is filled. This compact arrangement allows the maintenance of a uniform and low level of suction while still achieving a collection volume comparable to prior art devices in a container having dimensions as much as ten or twenty percent smaller. The resulting reduction in size is considered a significant safety factor in view of the high incidence of knocking over that occurs in a clinical setting.

BRIEF DESCRIPTION OF THE DRAWINGS

These and other features of the invention will be understood from the description and claims below, taken together with the drawings, wherein

FIG. 5 shows an internal element of the poppet assembly;

FIG. 6 and 6A illustrate details of a suction meter; and

DETAILED DESCRIPTION

Figure 1:
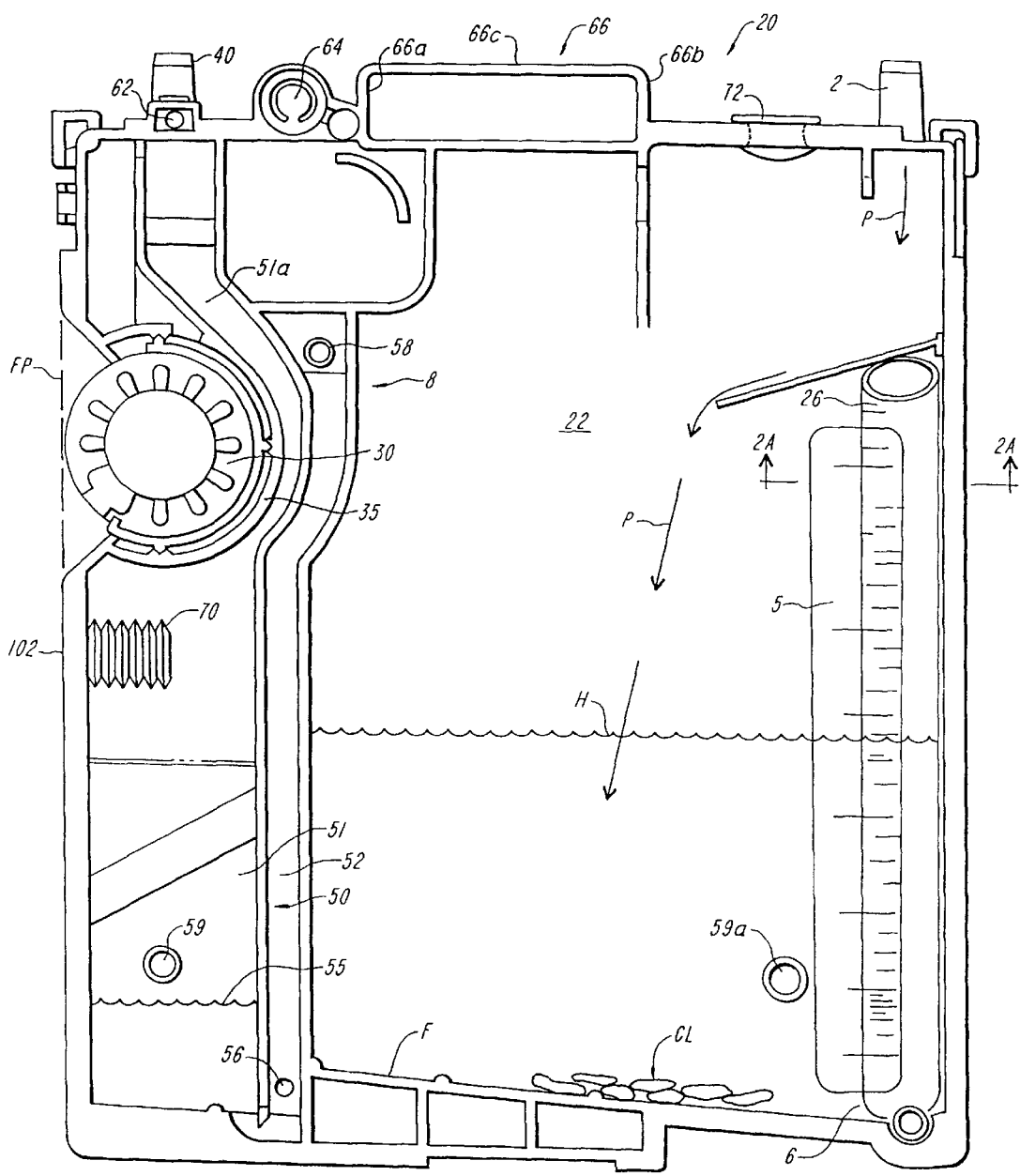
FIG. 1 is a face view of a chest drain in accordance with the present invention.
Figure 2:
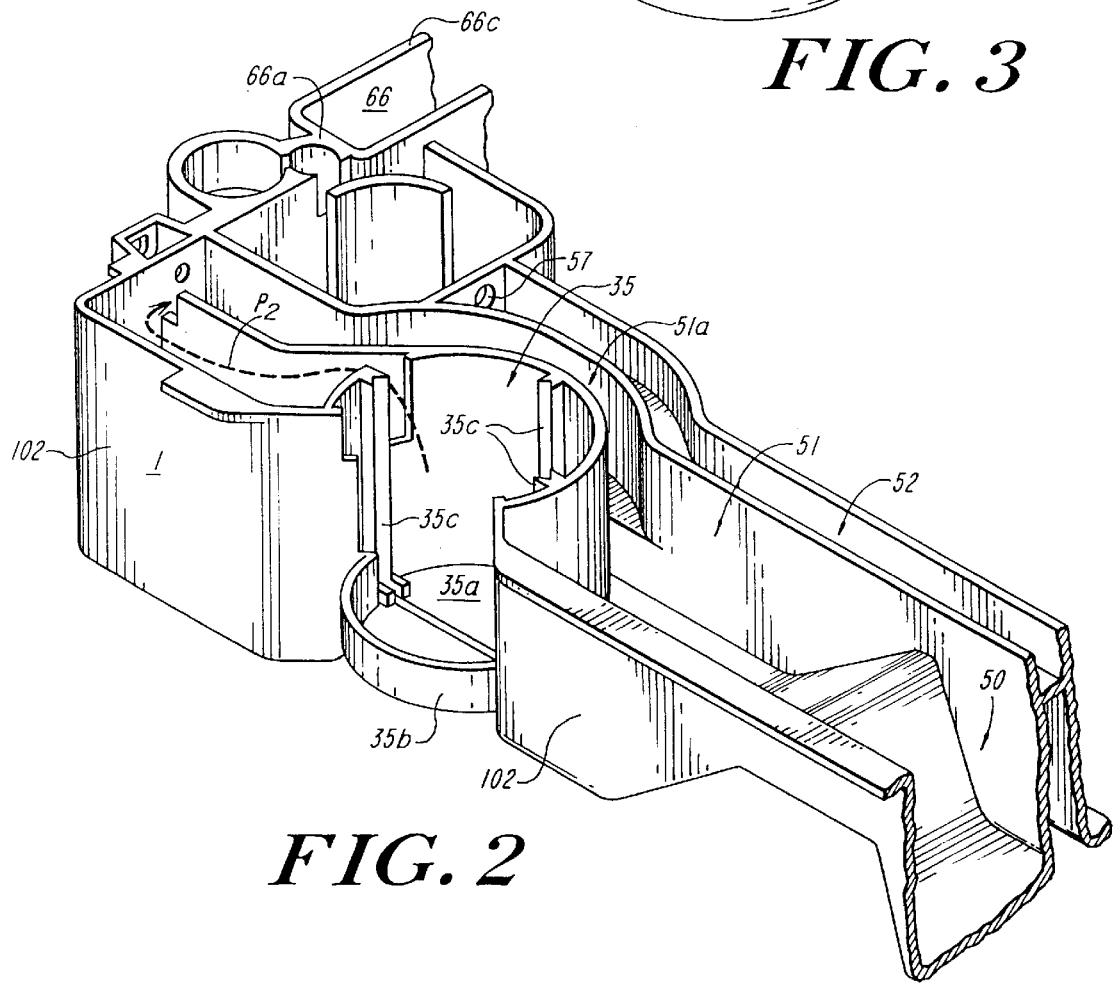
FIG. 2 is a detail of the housing portion of the chest drain of FIG. 1.

The embodiment of FIG. 1 is a so-called dry drain, in which the suction assembly 8 includes a suction setting valve 30 fitted within a recess 35 that controls the amount air entering the chamber to an amount which reduces to a user-set level of minus 15–20 cm $H_2O$, the amount of suction applied by a wall-fitting suction port 40. A water seal column 50 operates in a conventional manner as a one-way valve between the suction regulator and the fluid collection chamber 22. Water seal 50 includes a first or large column 51 and a second or narrow column 52 in which a pooling region 55 of approximately several centimeters of water act as a one way check valve for flow of air out of the collection chamber. In this embodiment, a float ball 56 rides up and down in the column 52 to indicate the level of excess suction prevailing in chamber 22. Briefly when suction in chamber 22 exceeds the level of suction applied by the suction regulator 30, the water level in column 52 rises and the position of the float ball 56 thus warns an attendant of dangerous conditions of excessive negativity. At the top of column 52, a check ball 58 positioned below a non-mating aperture 57 (FIG. 2) rises on the water and impedes the further rise of water level so that the pool of sealing water 55 cannot become entirely depleted, while water leaking past the check ball harmlessly collects above the ball and ultimately returns to the column when suction again reaches normal levels. Preferably, the leaky check ball 58 is configured to self-release after a short time interval, as described in commonly-owned earlier U. S. Pat. No. 5,114,416.

The water seal chamber 50 maybe filled directly through the suction inlet 40 which, as illustrated, is located directly above column 51. The upper region of column 51 curves around as shown at 51a about the portion of the housing which receives the suction regulator mechanism. While only a centimeter or two of water is required in the pooling region 55 to form an effective seal, the indicator ball 56 employs a column 7 to 8 inches high to meter the exact level of excess negativity in the chamber, up to 20 centimeters, requiring a height of about 10 inches to accommodate the illustrated column, and this constraint results in the vessel having a more or less conventional size and shape, although it may be smaller than a prior art drain of the same collection capacity. This is due, in part, to the compact transverse regulator location with the over/under seal configuration, allowing a relatively wider and lower collection volume. In other embodiments, the water seal and float valve may be replaced by an entirely dry flap assembly of valves or similar controls making the suction regulation unit even more compact, than illustrated for example in FIG. 1. In other embodiments, however, the dry suction regulator may be replaced by a water column set up to provide regulation of suction to a level set by the height of the water column, as illustrated in greater detail in each of applicant's; aforesaid U.S. patents, or applications identified herein and their respective parent or grandparent applications.

Other features appearing in the drawing include a positive pressure relief valve 62, which is a simple check valve at the top of the large water seal arm 51, and an excess negativity valve 64 which provides a compensating air inlet via a valved filtered passageway to the atmosphere through the top wall above the water seal small arm portion 52. Each of these assemblies are described in greater detail in Applicant's; commonly-owned U.S. Pat. No. 5,397,299. Pierceable septa 59, 59a allow one to conveniently sample or refill the water seal, and to sample collected fluid, respectively. A handle 66 is formed integrally with the body, and like the rest of the body extends to a common plane lying at the front face of the vessel, which is sealed to a transparent face plate that closes the assembly. The handle 66 is thus secured to the body by its vertical edges 66a and 66b, as well as welded to the face plate along both of those edges and along its upper horizontally-oriented face 66c thus forming an open rectangular box closed on five of its six sides. This forms an exceptionally secure and strong handle assembly which is relatively immune to snagging on dangling sheets or straps. A removable plug or grommet 72 in the upper surface of the vessel allows one to readily empty residual contents for separate disposal of the device and of the biological waste contained therein, after use. A bellows-type pressure indicator 70 is located in the water seal U-column, above the pooling region of the water seal chamber in column 51, and has its interior communicating with the surrounding atmosphere, so that it expands in length as the level of suction increases in the column 51.

Figure 1A:
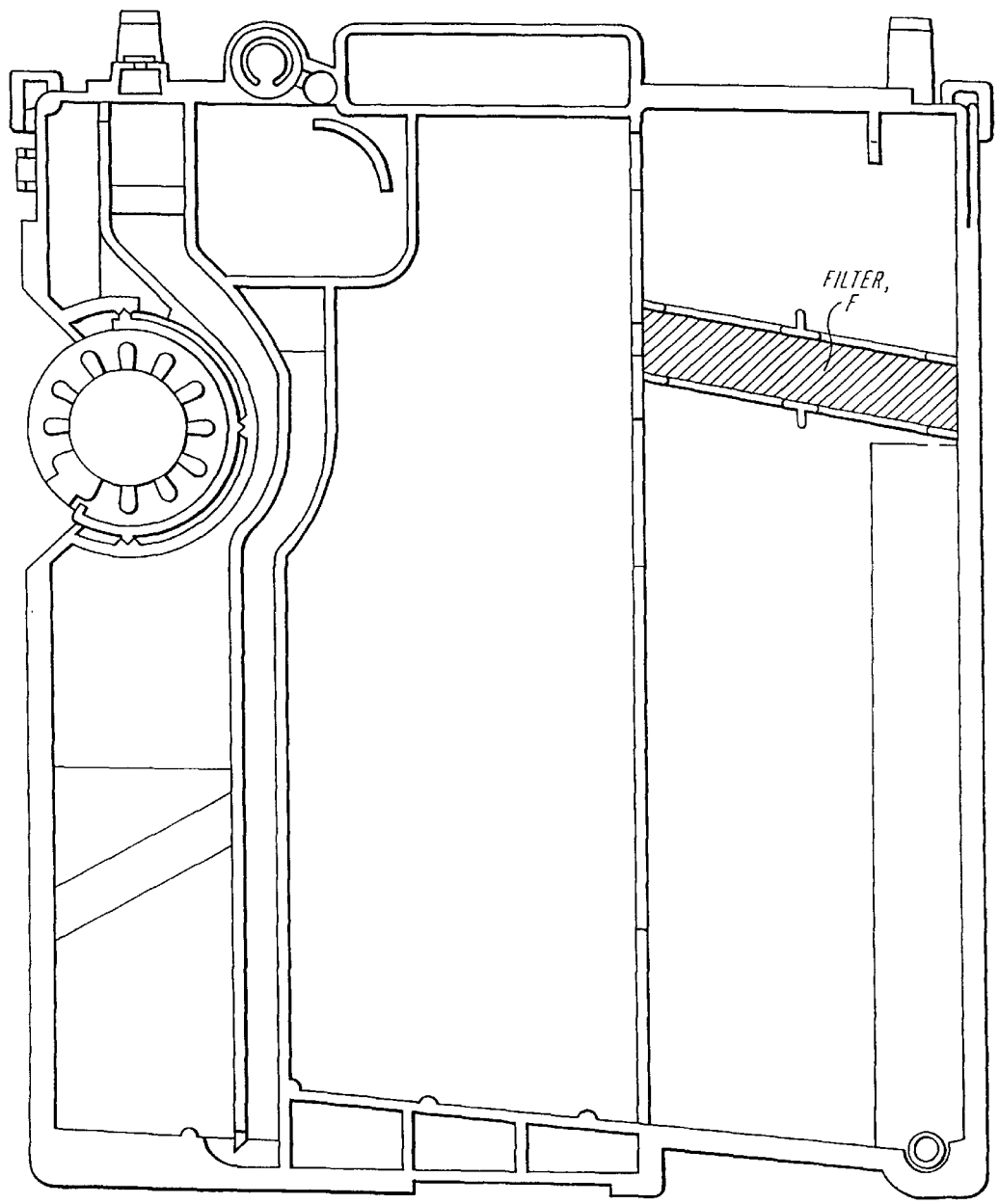
FIG. 1A and 1B show other embodiments.
Figure 1B:
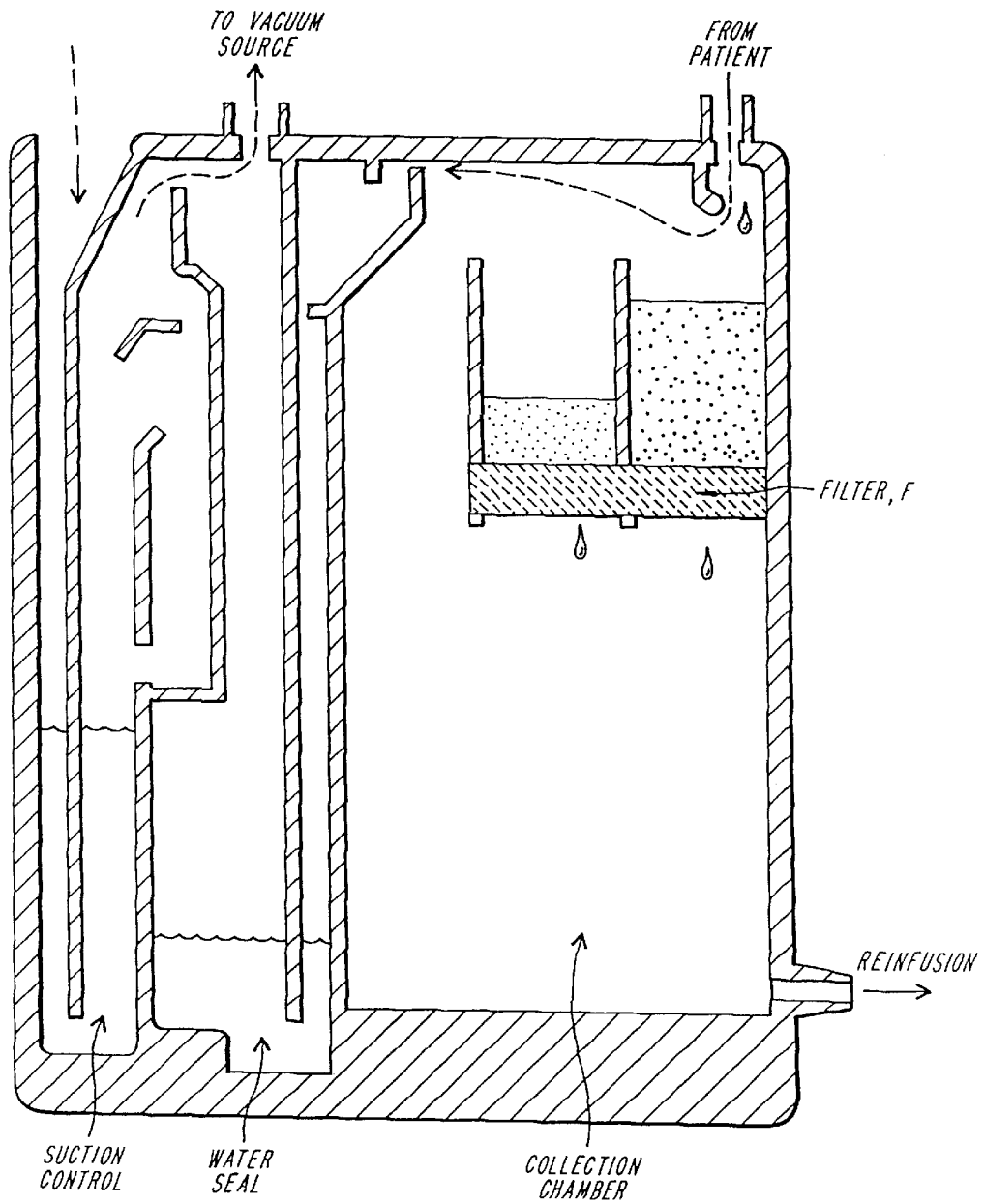
Figure 3:
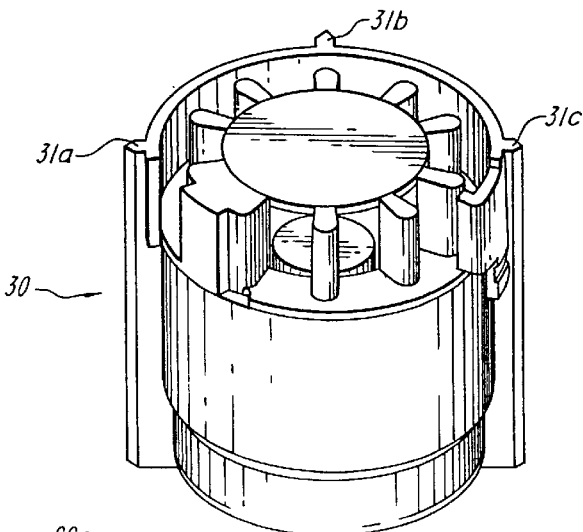
FIG. 3 is a detail of a poppet suction valve employed in the drain of FIGS. 1 and 2.

The device further includes a blood filter located below the inlet which isolates the clots so they cannot reach an infusion outlet of the collection chamber. The filter may be a basket-like large area filter assembly, a coarse screen which extends as a barrier in the collected fluid to segregate clots, or may be another filter arrangement. Examples of such embodiments are give in the aforesaid contemporaneously-filed patent application for Filtered Blood Collection Device, as well as in the aforesaid patents. In general, the filter is both large in area, and is "non-traumatic" in its action on the collected blood cells. FIGS. 1A and 1B show alternative embodiments with the filter locations being denoted by "F" . These filters include drop-through and overflow paths, or vent arrangements or other configurations to avoid trauma to or drying of blood cells from impact, pressure differentials, closed accumulation stagnation or the like.

A face plate is joined to the front of a substantially single-piece molded body to form the overall device, with the face plate lying substantially in a plane contacting each raised wall of the molded body, covering and closing the various columns, chambers and the like to form distinct subcompartments of the collection vessel. This face plate, while not specifically illustrated in FIG. 1, extends generally coincident with or slightly beyond the edges of the body portion, extending up to or above the highest surface 66c of the handle, to which it is joined, and extending on the left to the line marked "FP" which covers and generally shields the suction regulator 30 from inadvertent rotation. Further details of the mechanical and structural arrangements in this region are discussed later below, in connection with FIGS. 7 and 7A.

Initially, however, it bears noting that the molded housing or body portion 1 (FIG. 1) curves inwardly on its left side to form a cup-shaped recess 35 behind the face plate, which has a generally cylindrical shape with a floor 35a and a raised rim or bezel 35b into and against which the suction valve 30 fits. A plurality of thin V-channels 35c extend parallel to the axis of the cylindrical recess, and corresponding knife-edge ridges 31a, 31b and 31c protrude from the suction regulator body and fit into the channels to align and seal the regulator in the recess. The regulator, together with the adjacent upper and lower portions of the left wall of the device, combine to form the outer surface of the vessel, the volume inside of which communicates along a direct passage with the suction connector 40. The regulator thus drops transversely into the body, and in normal operation is oriented horizontally, with the various columns 51, 52 extending substantially vertically and curving around the regulator to reach to the top the vessel.

Figure 4:
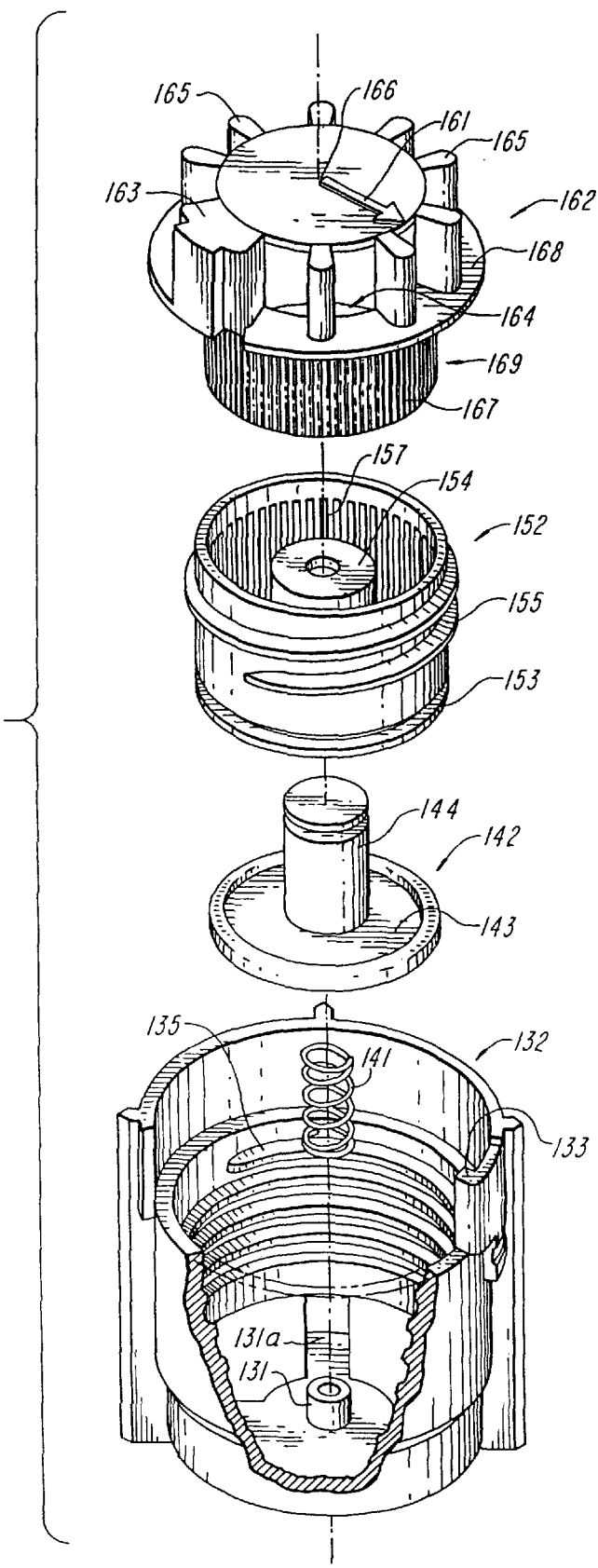
FIG. 4 is an exploded view showing construction of the poppet valve of FIG. 3.

As best seen in the exploded view, FIG. 4, the principal elements of suction regulator 30 include the body 132, the poppet 142 which is shaped generally like a top hat with a brim 143 extending about an inverted cup-shaped member 144, an upper body sleeve 152 and a control knob 162 which are arranged one above the other in the order described. The poppet 142 fits over a spring 141 held on a centering post 131 at the bottom of the body, which in turn is supported and centered by a skeletal frame formed of braces 131a, of which one is visible in the FIGURE. Thus the poppet is held in space across the generally open cylinder defined by the regulator as a whole.

The top 144 of the poppet 143 rides as a piston within a bore 154a defined by a centering cup 154 which extends above the lower end of sleeve 153, with the cup 154, like pin 131, being centrally supported by a screen, grid work or, as shown, a perforated plate 156 (FIG. 5). The poppet is thus axially suspended to respond to suction such that the brim 143 is normally urged by the compressed spring against the rim 153 of the sleeve, and is drawn down against the spring force to open a peripheral passageway which accommodates a large airflow to bleed down the suction in the vessel.

Continuing with a description of the suction regulator, the upper sleeve portion has a coarse external screw thread 155 about its periphery that mates with a corresponding internal screw thread 135 formed in the body 132, so that the rotational angle of sleeve 152 with respect to body 132 determines its height in the assembly. Since the sleeve bears against the brim 143 of the poppet, this also determines the resting state spring compression force, hence the suction response, of the assembly.

The inside surface of sleeve 152 is provided with a regular series of vertical ridges 157 which mate with a corresponding plurality of splines 167 on the cylindrical exterior of knob 162. Thus, knob 162 may be dropped into the sleeve at a desired angular orientation, and thereafter grips the sleeve firmly to transmit rotational torque thereto. Turning the knob 162 therefore adjusts the poppet release force.

Knob 162 has a plurality of radially oriented vanes or gripping teeth 165 disposed at its upper portion about a generally hub-like central plate 166 and a lower ring-like body annulus 168 from which a generally cylindrical key body 169 bearing the splines 167 extends. Adjacent pairs of teeth 165 define corresponding entryways leading directly into the hollow center 164 of the cylindrical body 169, so that the entire assembly 162, 152, and 132 form an open or porous body, except for the solid poppet which seats against the rim 153 of the cylindrical side wall of sleeve 152. Thus, as the poppet moves, air enters with little resistance and the suction level is immediately and dependably modulated by the floating poppet assembly.

A stop 163 is positioned on the annulus 168 and extends radially beyond the teeth 165 to abut against a protruding lip 133 of the body 132, thus limiting the total rotation of the knob 162 when it is inserted in the threaded sleeve 152 to slightly less than one full revolution. This defines the limits of the range of operation of the device on either side of the set point initially set by threading the sleeve into the body to compress the spring. If calibrated operation is desired, once the regulator has been assembled, a marker or arrow 161 may be adhesively affixed to the central plate 166 to point to a fixed circumferential set of graduations printed on the face plate of the drain device.

Figure 7:
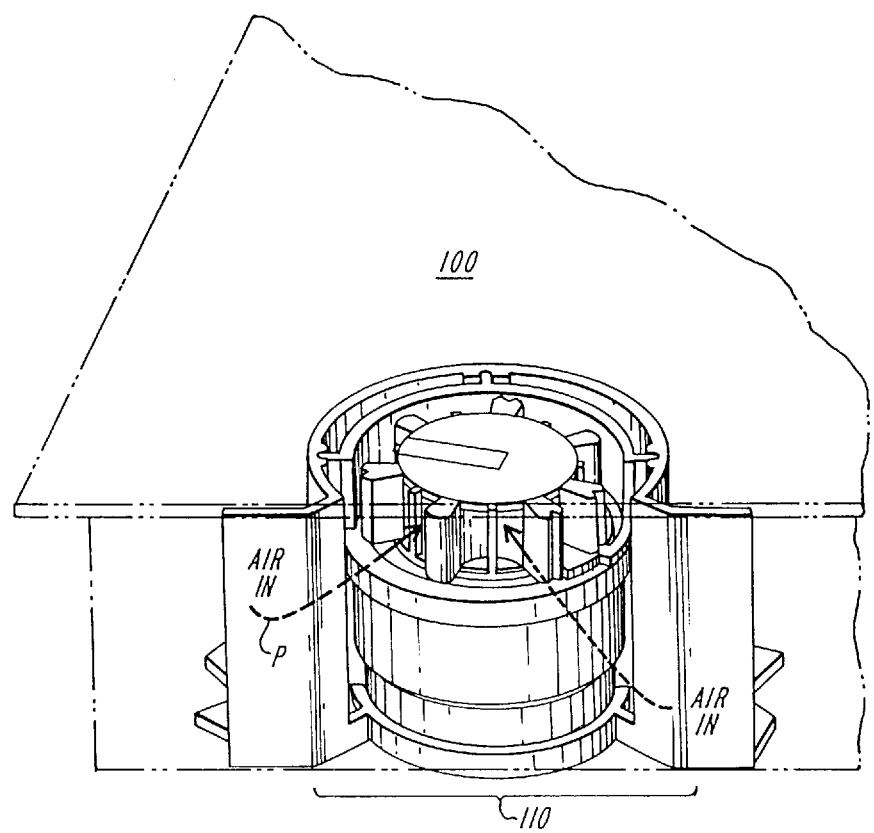
FIGS. 7 and 7A show further details of regulator mounting and operation.
Figure 7A:
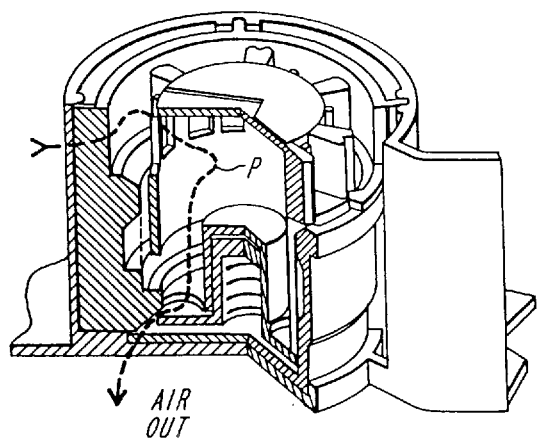

FIGS. 7 and 7A indicate the air entry paths through the regulator 30. A broad recessed area 110 in the generally vertically oriented left side wall 102 of the device curves inwardly toward the suction regulator 30 and is generally shielded form occlusion by the protruding left edge of the face plate 10 as well as the portions of wall 102 above and below the recess. Thus air readily enters between vanes 165 into the hollow center 164. A porous foam filter body may be fitted in region 164 to filter incoming air and assure that liquid or solid matter do not fall into the device or reach into the poppet assembly. Where suction level is lower than the set point, the poppet allows air through the cylindrical assembly along air entry path P, continuing by direct route along $P_2$ (FIG. 2) to the suction connection. This dependably maintains the net applied suction level at the set point in the 10–50 cm $H_2O$ range.

The level of suction prevailing in the water seal assembly is shown by a nonmechanical meter formed by the passively-operated bellows 70 (FIG. 1). As shown in greater detail in FIG. 6 the bellows 70 is a pleated polymer tube which has one end-the right end as shown-closed, and its open end 71 sealably affixed to an opening in side wall 102 by a grommet 73. The outside of the bellows thus experiences the suction prevailing in seal 50, and it extends along a substantially horizontal line B behind the face plate in a left-right direction with its extension increasing as a greater degree of suction is applied.

Applicants have found that this bellows meter, while providing a repeatable and accurate response, suffers from a low degree of "readability" due to factors such relative parallax effects, the jagged nature of its wall geometry, glare of the face plate as well as the generally oblique perspective occasioned by such chest drains being normally located well below eye level near or on a bedside or floor. The visibility problem is addressed in accordance with another aspect of the invention by providing a graduation pattern on the face plate which intersects the expanding bellows 70.

One such pattern 80 is shown in FIG. 6 employing an elbow-shaped clear space in the face plate 100 and having suction readings 82 arrayed along its curving edge. The bellows 70 advances along a straight portion of the visible path, and as it advances further the graduations are swept across the bellows, which is colored a contrasting color to the face graduations. The intersection of the bellows right end with a crossing line thus defines more accurately and visibly the prevailing degree of suction.

Another pattern 85 is shown in FIG. 6A. Here an elbow-shaped space above the bellows curves down into the bellows extension path. At lesser suctions a small side fragment or wedge of the bellows tip is visible while an increasingly broader vertical width of the bellows becomes visible as higher degrees of suction are reached. The bellows cross the vertical graduation line at saturation, i.e., at the highest degree of suction, corresponding to −40 cm $H_2O$ with the illustrated scale. Notably, the vertical line is less prone to parallax errors when viewed aslant from above in normal operation. Other curved or oblique graduation patterns adjacent the extension path B are also contemplated to provide a shaped display or oblique edge crossing effect. This allows the simple expansion bellows to reliably indicate the degree of suction set on and achieved by the regulator 30.

The invention has been described with reference to several particular embodiments; however, it may take other forms which will occur to those skilled in the art, and all such forms are encompassed within the spirit and scope of the present invention, and its equivalent, as defined by the claims appended hereto.

What is claimed is:

1. The blood collection device comprising a vessel having a body closed by a face plate, a collection chamber with a collection tube attached to said collection chamber, a suction connector for attaching to a source of suction to place the collection chamber in suction communication therewith, and an adjustable pressure regulator valve assembly having a poppet therein, wherein said assembly being sealingly fitted as a preassembled unit into a recess formed in said vessel and having a valve body defining an air intake passage communicating through said valve to control by mixing air, the level of suction in the vicinity of said suction connector to a level set by said valve for drawing fluid into said collection chamber at a controlled suction level, wherein said valve when fitted in said recess is accessible from outside the vessel for adjustment over a range of suction with a preset end point.

2. The blood collection device according to claim 1, wherein said adjustable pressure regulation valve comprises a canister forming said air intake.

3. The blood collection device according to claim 1, further comprising a filtered intake for filtering air entering the vessel.

4. The blood collection device according to claim 2, wherein said face plate forms a front wall of said collection chamber, and said recess in said vessel is located behind said front wall said canister defining an air inlet passage shielded by said face plate from interference.

5. The blood collection device according to claim 1, wherein the collection chamber is formed by a molded body having a top, a back and sides, said molded body being attached to said face plate to result in a fluid tight volume, and said molded body having a protruding band across a portion of its top, said band forming a boxed-in handle.

6. The blood collection device according to claim 2, wherein said canister is mounted in an upper side portion of said device, and further comprising a seal chamber located below said canister and communicating with said suction hose fitting and with said collection chamber.

7. The blood collection device according to claim 2, wherein said poppet is supported on a compression spring and said canister includes a threaded sleeve for setting extension of said compression spring to determine an operating suction value.

8. The blood collection device according to claim 7, wherein said relief valve includes a fluted knob for gripping said sleeve, said fluted knob being slideably fitted into said sleeve to set a stop range of said sleeve and being thereafter irremovably secured in said sleeve by said face plate.

9. The blood collection device according to claim 1, wherein said adjustable pressure regulation valve includes an adjusting wheel rotatable through less than one full revolution and operative to vary operating suction level within the range of approximately −10 and −50 cm $H_2O$.

10. A chest drain having a molded body and a face plate which together define a vessel with an interior including at least one collection chamber, a contoured recess formed inside said molded body, a fluid inlet port and a suction inlet port for attaching to a source of suction to place the collection chamber in suction communication therewith, and also having a preassembled suction regulator assembly, wherein said preassembled suction regulator assembly being fitted into said contoured recess of said body as a unit and secured between said body and said face plate to form an air inlet passageway through said assembly for setting an effective suction level in said interior.

11. The chest drain device according to claim 10, further comprising a top, back and sides, wherein said body has a protruding band extending across a portion of said top and forming a compartment thereabove.

12. A suction regulation assembly for attachment to a blood collection chamber, wherein the assembly comprises a vessel body, a suction connector for attaching to a source of suction to apply said suction to said vessel body and an adjustable pressure regulation valve sealingly fitted as a preassembled unit into a contoured recess formed in said vessel body and having a valve body defining an air passage communicating from outside said vessel body through said valve to control, by mixing air, the level of suction in the vicinity of said suction connector to a level set by said valve for application of a controlled suction level to said chamber, wherein said valve when fitted in said recess is accessible from outside the suction regulation assembly for adjustment over a range of suction with a preset end point.

13. A suction regulation assembly according to claim 12, wherein a face plate closes said vessel body and secures said pressure regulation valve in said contoured recess.

14. A collection device including a body having top, back and sides, and also including a face plate closing said body to result in a fluid-tight interior forming a suction chamber for drawing in and holding fluid, wherein said device includes a preassembled valve with an air inlet path for allowing air into said device in a controlled manner effective to set and maintain a substantially constant level of suction in said chamber, and a filter in said inlet path for filtering air as it enters said air inlet path.

* * * * *